United States Patent
Krosney

(10) Patent No.: US 11,779,675 B2
(45) Date of Patent: Oct. 10, 2023

(54) AIR STERILIZATION INSERT FOR HEATING, VENTILATION, AND AIR CONDITIONING (HVAC) SYSTEMS

(71) Applicant: Molekule Group, Inc., Palm Beach Gardens, FL (US)

(72) Inventor: Mark D. Krosney, South Glastonbury, CT (US)

(73) Assignee: Molekule Group, Inc., Palm Beach Gardens, FL (US)

( * ) Notice: Subject to any disclaimer, the term of this patent is extended or adjusted under 35 U.S.C. 154(b) by 0 days.

(21) Appl. No.: 17/073,658

(22) Filed: Oct. 19, 2020

(65) Prior Publication Data
US 2022/0120454 A1    Apr. 21, 2022

(51) Int. Cl.
*A61L 9/20* (2006.01)
*F24F 13/00* (2006.01)
*F24F 110/50* (2018.01)
*F24F 8/22* (2021.01)

(52) U.S. Cl.
CPC ............... *A61L 9/20* (2013.01); *F24F 13/00* (2013.01); *A61L 2209/12* (2013.01); *A61L 2209/16* (2013.01); *F24F 8/22* (2021.01); *F24F 2110/50* (2018.01); *F24F 2203/00* (2013.01)

(58) Field of Classification Search
None
See application file for complete search history.

(56) References Cited

U.S. PATENT DOCUMENTS

| | | | |
|---|---|---|---|
| 5,225,167 | A | 7/1993 | Wetzel |
| 5,505,904 | A | 4/1996 | Haidinger et al. |
| 5,626,820 | A | 5/1997 | Kinkead et al. |
| 5,689,364 | A | 11/1997 | McGregor et al. |
| 5,761,908 | A | 6/1998 | Oas et al. |
| 5,964,792 | A | 10/1999 | Augustine |

(Continued)

FOREIGN PATENT DOCUMENTS

| | | |
|---|---|---|
| CN | 101437342 A | 5/2009 |
| CN | 101639267 A | 2/2010 |

(Continued)

OTHER PUBLICATIONS

1st Examination Report received from the Saudi Patent Office in related Saudi Arabia Patent Application No. 516370810 dated Nov. 13, 2017.

(Continued)

*Primary Examiner* — Andrew Smyth
(74) *Attorney, Agent, or Firm* — THE MARBURY LAW GROUP, PLLC

(57) ABSTRACT

An airflow sterilizing unit configured to airflow in a heating, ventilation, and air conditioning (HVAC) system is disclosed. The airflow sterilizing unit includes a portion of a duct at least partially lined with an ultraviolet (UV) reflective material, a plurality of hollow structures positioned within the portion of the duct, each comprising an external UV reflective surface, and at least one array of UV light emitting diodes (LEDs) mounted on a surface of at least one of the plurality of hollow structures. The sterilizing unit is configured to replace a section of an existing duct in the HVAC system such that air within the HVAC system passes through the sterilizing unit before exiting from one or more vent.

12 Claims, 5 Drawing Sheets

(56) References Cited

U.S. PATENT DOCUMENTS

| | | |
|---|---|---|
| 6,039,926 A | 3/2000 | Goldman |
| 6,053,968 A | 4/2000 | Miller |
| 6,171,548 B1 | 1/2001 | Rose et al. |
| 6,254,337 B1 | 7/2001 | Arnold |
| 6,322,614 B1 | 11/2001 | Tillmans |
| 6,464,760 B1 | 10/2002 | Sham et al. |
| 6,541,777 B1 | 4/2003 | Lombardo et al. |
| 6,797,044 B2 | 9/2004 | Ou Yang et al. |
| 6,893,610 B1 | 5/2005 | Barnes |
| 6,949,223 B2 | 9/2005 | McEllen |
| 7,175,814 B2 | 2/2007 | Dionisio |
| 7,303,612 B2 | 12/2007 | Morrow et al. |
| 7,498,004 B2 | 3/2009 | Saccomanno |
| 8,236,236 B2 | 8/2012 | Garner |
| 8,980,178 B2 | 3/2015 | Gaska et al. |
| 2002/0144601 A1 | 10/2002 | Palestro et al. |
| 2003/0170151 A1 | 9/2003 | Hunter et al. |
| 2005/0000365 A1 | 1/2005 | Nelsen et al. |
| 2005/0078473 A1 | 4/2005 | Zuloff |
| 2005/0163646 A1 | 7/2005 | Liang |
| 2005/0163648 A1 | 7/2005 | Liang |
| 2005/0173352 A1 | 8/2005 | Burrows et al. |
| 2005/0242013 A1 | 11/2005 | Hunter et al. |
| 2006/0042210 A1 | 3/2006 | Dallas et al. |
| 2006/0159594 A1 | 7/2006 | Parker et al. |
| 2007/0101867 A1 | 5/2007 | Hunter et al. |
| 2007/0102280 A1* | 5/2007 | Hunter ............... A61L 9/16 422/186.3 |
| 2007/0196235 A1 | 8/2007 | Shur et al. |
| 2008/0095661 A1 | 4/2008 | Kohler |
| 2009/0004047 A1 | 1/2009 | Hunter et al. |
| 2009/0041632 A1 | 2/2009 | Day et al. |
| 2009/0084734 A1 | 4/2009 | Yencho |
| 2009/0098014 A1 | 4/2009 | Longstaff |
| 2009/0252646 A1 | 10/2009 | Holden et al. |
| 2010/0128901 A1 | 5/2010 | Herman |
| 2010/0132715 A1 | 6/2010 | Litz |
| 2010/0143205 A1 | 6/2010 | Engelhard |
| 2010/0260644 A1 | 10/2010 | Day et al. |
| 2010/0279595 A1* | 11/2010 | Horstman ............. B64D 13/06 454/339 |
| 2011/0033346 A1 | 2/2011 | Bohlen et al. |
| 2012/0118150 A1 | 5/2012 | Brizes et al. |
| 2012/0168641 A1 | 7/2012 | Lizotte |
| 2012/0273340 A1 | 11/2012 | Felix |
| 2012/0285459 A1 | 11/2012 | Sata et al. |
| 2013/0238042 A1 | 9/2013 | Gildersleeve et al. |
| 2013/0313104 A1 | 11/2013 | Yates et al. |
| 2014/0017135 A1* | 1/2014 | Boodaghians .......... A61L 9/205 422/121 |
| 2014/0030144 A1 | 1/2014 | Krosney et al. |
| 2014/0271374 A1 | 9/2014 | Giles et al. |
| 2014/0348701 A1 | 11/2014 | Kirschman |
| 2016/0001108 A1 | 1/2016 | Zhou et al. |
| 2016/0038624 A1 | 2/2016 | Krosney |
| 2017/0000916 A1 | 1/2017 | Stibich et al. |
| 2017/0202988 A1 | 7/2017 | Clark |
| 2017/0296690 A1 | 10/2017 | Matsui et al. |
| 2017/0307234 A1* | 10/2017 | Matschke ............. A61L 2/10 |
| 2018/0021471 A1 | 1/2018 | Krosney |
| 2019/0084852 A1* | 3/2019 | Harris ............... C02F 1/78 |
| 2019/0160190 A1 | 5/2019 | Kreitenberg |
| 2020/0108166 A1 | 4/2020 | Rhoden |
| 2020/0144601 A1 | 5/2020 | Takahashi et al. |
| 2020/0230267 A1* | 7/2020 | Greenfield .......... B01J 19/0066 |
| 2020/0254133 A1* | 8/2020 | Carr .................. F24F 8/192 |
| 2021/0298391 A1 | 9/2021 | Keene et al. |

FOREIGN PATENT DOCUMENTS

| | | | |
|---|---|---|---|
| CN | 202198889 U | 4/2012 | |
| CN | 203980497 U * | 12/2014 | |
| CN | 203980947 | 12/2014 | |
| CN | 205181843 | 4/2016 | |
| CN | 205181843 U * | 4/2016 | |
| CN | 111093822 | 5/2020 | |
| CN | 111093822 A * | 5/2020 | ............... A61L 2/10 |
| DE | 199 43 876 A1 | 3/2001 | |
| EP | 2554583 A1 | 2/2013 | |
| EP | 2921183 A1 | 9/2015 | |
| JP | H6-12773 U | 2/1994 | |
| JP | 11-014130 A | 1/1999 | |
| JP | 2000-008178 A | 1/2000 | |
| JP | 2000-070928 A | 3/2000 | |
| JP | 2001-224672 A | 8/2001 | |
| JP | 2001-293072 A | 10/2001 | |
| JP | 2001520552 A | 10/2001 | |
| JP | 2003-088571 A | 3/2003 | |
| JP | 2004504869 A | 2/2004 | |
| JP | 2005-166180 A | 6/2005 | |
| JP | 2005-203437 A | 7/2005 | |
| JP | 2005-253799 A | 9/2005 | |
| JP | 2007-511279 A | 5/2007 | |
| JP | 2008-259809 A | 10/2008 | |
| JP | 2009-22903 A | 2/2009 | |
| JP | 2009-181914 A | 8/2009 | |
| JP | 2009-532200 A | 9/2009 | |
| JP | 2011-530542 A | 12/2011 | |
| JP | 2012-512723 A | 6/2012 | |
| JP | 2012533720 A | 12/2012 | |
| JP | 5432286 B2 | 12/2013 | |
| JP | 2016530918 A | 10/2016 | |
| KR | 10-2000-0017005 A | 3/2000 | |
| KR | 20000017005 A | 3/2000 | |
| KR | 20-0315033 | 5/2003 | |
| KR | 200315033 | 5/2003 | |
| KR | 1020190000715 | 1/2019 | |
| WO | 98/47545 A2 | 10/1998 | |
| WO | 02/04036 A1 | 1/2002 | |
| WO | 2005/011753 A1 | 2/2005 | |
| WO | 2007113537 A1 | 10/2007 | |
| WO | 2010071814 A1 | 6/2010 | |
| WO | 2011087100 A1 | 7/2011 | |
| WO | 2012166131 A1 | 12/2012 | |
| WO | 2015131243 A1 | 9/2015 | |
| WO | 2016081703 A1 | 5/2016 | |
| WO | WO-2016081703 A1 * | 5/2016 | ............... A61L 2/10 |
| WO | 2017070359 A1 | 4/2017 | |
| WO | 2020151918 A1 | 7/2020 | |

OTHER PUBLICATIONS

Extended European Search Report from the European Patent Office in related Application No. 14829593.4-1370 /3024503 in International Application No. PCT/US2014/048144 dated Feb. 2, 2017.

International Search Report and Written Opinion of the International Searching Authority in International Application No. PCT/US2016/057932 dated Feb. 3, 2017.

International Preliminary Report on Patentability received from the Korean Intellectual Property Office in related International Application No. PCT/US2018/024229 dated Dec. 19, 2019.

First Examination Report (FER) received from the Indian Patent Office in related Indian Patent Application No. 201637004406 dated Oct. 25, 2020.

International Preliminary Report on Patentability received from the Korean Intellectual Property Office in related International Application No. PCT/US2016/057932 dated Feb. 1, 2018.

International Preliminary Report on Patentability and Written Opinion of the International Searching Authority in related International Application No. PCT/US2018/024229 dated Jul. 13, 2018.

International Search Report and the Written Opinion of the International Searching Authority received in related Application No. PCT/US2018/024229 dated Jul. 13, 2018.

Extended European Search Report received from The Hague Patent Office in related European Application No. EP 16 85 8222 dated May 22, 2019.

European Communication Pursuant to Rules 70(2) and 70a(2) EPC from the European Patent Office in related European Application No. EP 16 85 8222 dated Jun. 7, 2019.

(56) References Cited

OTHER PUBLICATIONS

First Notification of Reasons for Refusal received from the Japanese Patent Office in related Japanese Patent Application No. 2016-530064 dated May 31, 2018.
First Notification of Reasons for Refusal received from the Japanese Patent Office in related Japanese Patent Application No. in JP 2018-540690 dated Sep. 3, 2020.
Written Opinion of the International Preliminary Examination Authority received in related Application No. PCT/US2018/024229 dated Oct. 24, 2019.
1st Office Action received from the European Patent Office in related European Patent Application No. 14 829 593.4-1104 dated Nov. 6, 2020.
International Search Report and the Written Opinion of the International Searching Authority received from the Korean Intellectual Property Office in related International Application No. PCT/US2018/024228 dated Jul. 13, 2018.
International Preliminary Report on Patentability received from the Korean Intellectual Property Office in related International Application No. PCT/US2018/024228 dated Dec. 16, 2019.
International Preliminary Report on Patentability and Written Opinion of the International Searching Authority in related International Application No. PCT/US2021/033752 dated Sep. 16, 2021.
Extended European Search Report received in related European Patent Application No. 18851780.9-1104 / 3675919 PCT/US2018/024228 dated May 27, 2021.
Decision of Refusal received in related Japanese Patent Application No. 2018-540690 dated Jul. 1, 2021.
Japan Patent Office, Notice of Reasons for Refusal in Japanese Patent Application No. JP 2020-534160, including English-language translation, dated Jan. 3, 2022, (7 pages).
Intellctual Property India, First Examination Report in corresponding Indian Patent Application No. 201837013736, and English-language translation, dated Aug. 25, 2020 (11 pages).
Saudi Authority for Intellectual Property, 1st Examination Report for PCT National Phase Application No. 518391412 and English-language translation, dated Sep. 22, 2021(10 pages).
Saudi Authority for Intellectual Property, 2nd Examination Report for PCT National Phase Application No. 518391412 and English-language translation, dated Feb. 16, 2022 (20 pages).
Korean Intellectual Property Office, International Search Report and Written Opinion in corresponding International Application No. PCT/US2021/050342 dated Dec. 31, 2021 (10 pages).
Intellectual Property India, First Examination Report issued in Indian Patent Application No. 202037007585, and English-language translation, dated Mar. 28, 2022 (7 pages).
Korean Intellectual Property Office, "International Search Report and Written Opinion," issued in related International Application No. PCT/US2021/055670, dated Jul. 15, 2022 (9 pages).
Japanese Patent Office, Reconsideration Report by Examiner before Appeal, issued in Japanese Patent Application No. 2018-540690, dated May 9, 2022, including English-language translation (4 pages).
Notification Concerning Transmittal of International Preliminary Report on Patentability received in related Patent Application No. PCT/US21/33752 dated Sep. 7, 2022.
Japanese Patent Office, Notice of Reasons for Refusal received in Japanese Patent Application No. 2018-540690 dated Aug. 30, 2022.
Japanese Patent Office, Decision of Refusal issued in related Japanese Patent Application No. 2020-534160 dated Jan. 27, 2022.
International Preliminary Report on Patentability for International Application No. PCT/US2014/48144 dated Feb. 4, 2016, 7 pages.
International Preliminary Report on Patentability for International Application No. PCT/US2021/050342 dated Jan. 9, 2023, 6 pages.
International Search Report and Written Opinion for International Application No. PCT/US2014/48144 dated May 14, 2015, 9 pages.
Saudi Patent Office, Final Decision rejection with partial English-language translation received in corresponding Saudi Patent Application No. 518391412 dated Sep. 16, 2022.
First Examination Report received for Saudi Arabia Patent Application No. 520411446, dated Dec. 28, 2022, 12 pages.
Office Action of Korean Patent Application No. 10-2020-7008612, dated Feb. 1, 2023, 13 pages.
Trial and Appeal Decision for Japanese Patent Application No. 2018-540690, mailed Jan. 26, 2023, 4 pages.
Notice of Preliminary Rejection received from the Korean Patent Office in related Patent Application No. 10-2020-7008612 dated Feb. 1, 2023.
International Preliminary Report on Patentability and Written Opinion for International Application No. PCT/US2021/055670, dated May 11, 2023, 6 pages.
Substantive Examination Report received for Saudi Arabia Patent Application No. 520411446, dated May 21, 2023, 14 pages.
Notice of Preliminary Rejection received from the Korean Patent Office for related Application No. 10-2018-7014409 dated Jul. 25, 2023.

\* cited by examiner

AIR STERILIZATION INSERT FOR HEATING, VENTILATION, AND AIR CONDITIONING (HVAC) SYSTEMS

BACKGROUND

There is a growing demand for improvements in indoor air quality in private and public settings to reduce the transmission of pathogens. Recent world events have demonstrated a need for sterilization of airborne pathogens, virus and bacteria. As information about the health risks related to exposure to various types of contaminants becomes available, interest in maintaining a healthy indoor environment has expanded to include residential and commercial settings. In particular, the presence of certain molds, bacteria, and/or viruses has been shown to cause long-lasting and far-reaching health problems. Consequently, prevention and treatment of indoor contaminants is of interest across industries as well as individuals.

Currently implemented approaches to reducing pathogens involve decontamination of room surfaces between occupancies. One potential solution may be to irradiate the room and all of its surfaces with high-level ultra-violet (UV) radiation. Another potential solution may be the spraying of the room with hydrogen peroxide mist. However, in both of these solutions, the room must be unoccupied and isolated. In the event a person desires to enter the room during the decontamination process, significant protective equipment must be worn by the individual. Further, separate units utilizing ultraviolet (UV) radiation, either alone or in combination with HEPA type filtering, may employ additional fans to create pressurized areas, and require installation of UV lights inside ventilation ducting.

Traditional airflow treatment devices have typically been large and difficult to locate optimally, with performance degrading substantially over time. Currently available compact systems may not provide adequate airflow and/or pathogen kill rate. Further, conventional UV-based systems may use fluorescent tube elements, for which maintenance and replacement of the UV tubes may prove to be a laborious process.

Radiation sources, such as UV lamps, have been used in portable air purification devices and HVAC systems to inhibit growth of bacteria and certain molds on condensing coils and/or drain pans. Filtering devices such as activated carbon filters, high energy particulate air (HEPA) filters, and electrostatic filters have been used to remove particulate matter and pollutants from indoor air. However, configuring individual probes, filters, or UV lamps in HVAC ductwork on an as-needed basis is time-consuming and expensive. For example, an HVAC specialist may be hired to install such ductwork components at recommended intervals (for example, every 15 feet (4.57 meters)), and then to install wiring to electrically connect each component to the building's main electrical system.

It would therefore be desirable to have an indoor air treatment apparatus that reduces or removes airborne pathogens and is designed for integration into an existing HVAC system. It is further desirable to have an indoor air treatment apparatus which can operate while a room or building is occupied. In particular, it would be desirable to have an air sterilization and/or purification system that is quiet, unobtrusive, and easy to maintain, while also being highly effective in the removal and/or neutralization of harmful airborne pathogens and in which performance does not significantly degrade over time and that is easy to maintain.

SUMMARY OF THE INVENTION

Systems, methods, and devices of various embodiments enable treatment of air circulating in a heating, ventilation, and air conditioning (HVAC) system by incorporating at least one sterilizing unit. In some embodiment systems, methods, and devices, the at least one sterilizing unit may include a portion of a duct at least partially lined with an ultraviolet (UV) reflective material, a plurality of hollow structures positioned within the portion of the duct, each comprising an external UV reflective surface, and at least one array of UV light emitting diodes (LEDs) mounted on a surface of at least one of the plurality of hollow structures. In some embodiment systems, methods, and devices, the sterilizing unit may be configured to replace a section of an existing duct in the HVAC system such that airflow within the HVAC system passes through the sterilizing unit before exiting from one or more vent. In some embodiments, a sterilizing unit may be fabricated as a module that may be inserted within existing HVAC ductwork. The sterilizing unit module may passively receive airflow from the existing HVAC system and irradiate the flowing air with UV light to irradiate potential pathogens, virus, and bacteria.

In some embodiment systems, methods, and devices, the at least one sterilizing unit may also include a power supply housed within at least one of the hollow structures. In some embodiment systems, methods, and devices, each of the at least one array of UV LEDs may be connected to a printed circuit board assembly (PCBA) within the hollow structure on which the array is mounted. In some embodiment systems, methods, and devices, the at least one hollow structure on which the at least one array of UV LEDs is mounted may be positioned at an end of the sterilizing unit upstream from an airflow exit point. In some embodiment systems, methods, and devices, the at least one array of UV LEDs may be configured to emit radiation at one or more wavelength within a range of 240-280 nm. In some embodiment systems, methods, and devices, the UV LEDs may be configured to irradiate the air within the HVAC system with a UV radiation dosage sufficient to reduce airborne pathogens.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE DRAWINGS

Figure 1A:
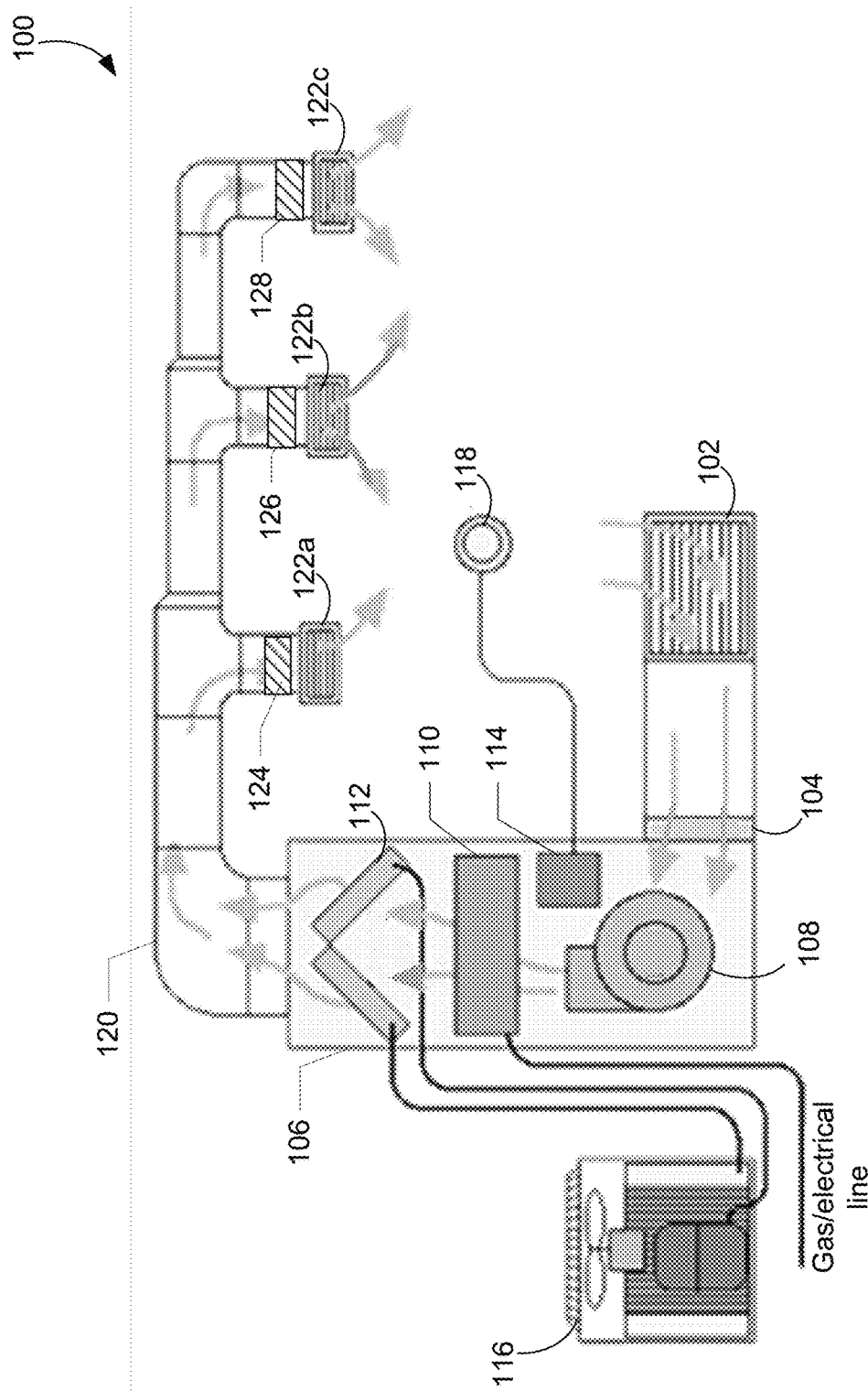
FIGS. 1A and 1B show representative diagrams of an HVAC system according various embodiments.

In the description and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "UV radiation" is used herein to mean high energy UV-C photons with wavelengths shorter than 290 nm, which are capable of traversing cellular walls. In various embodiments, the UV radiation utilized for air treatment may be at one or multiple wavelengths within the range of 200 to 320 nm range.

The terms "flux" and "radiation flux" are used herein to mean the amount of radiation at the specified wavelength that reaches the surface of airborne pathogens. The terms "dwell time" and "residence time" are used herein to refer to the duration of time that the airborne pathogens remain exposed to the radiation flux.

The terms "contaminants" is used herein to refer to impurities, including all of biological agents (e.g., pathogens), chemical agents, pollutant particles, volatile organic compounds, and chemical vapors.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1 The term "at most" followed by a number is used herein to denote the end of a range ending with that number (which may be a range having 1 or 0 as its lower limit, or a range having no lower limit, depending upon the variable being defined). When, in this specification, a range is given as "(a first number) to (a second number)" or "(a first number)-(a second number)," this means a range whose lower limit is the first number and whose upper limit is the second number.

While the specification concludes with claims defining the features of embodiments of the invention that are regarded as novel, it is believed that the invention will be better understood from a consideration of the following description in conjunction with the figures, in which like reference numerals are carried forward.

The various embodiments provide modular units containing arrays of light emitting diodes (LEDs) for treating an airflow circulating within a heating, ventilation, and air conditioning (HVAC) system in order to significantly reduce the number of contaminants therein. Such modular units allow for single installation with comparatively little effort, expense, and maintenance relative to conventional air stream decontamination techniques used in HVAC systems. For example, at least one sterilizing unit may include one or more array of UV LEDs capable of directing ultraviolet radiation within the air stream, thereby sterilizing microbes and halting their reproduction within the air stream.

In an embodiment, one or more sensor may be used to monitor air quality characteristics and/or equipment status. Air quality characteristics monitored may include, but are not limited to, airflow, temperature, humidity, and contaminant levels. Equipment parameters monitored may include, but are not limited to, UV LED performance. If an irregularity is noted, a monitoring system may automatically provide a notification to an indicator external to the HVAC system. In some embodiments, system controls may modify the operation of the sterilization unit based on the monitored indicators. For example, if the contaminant levels are monitored and determined to be well within healthful, safe levels, the UV LEDS may be turned off.

The sterilizing unit according to various embodiments may be installed into an existing HVAC system to eradicate pathogens in the output air of the HVAC system. The sterilizing unit may be located at the end of a ventilation duct where the air flows into a specific room or larger area. The sterilizing unit may be tailored to different duct sizes and discharge ducts depending on the HVAC system. For example, in some embodiments, a large sterilizing unit or multiple smaller units may be mounted near or coupled to the central air handler of an HVAC system.

The sterilizing unit of various embodiments is virtually silent, and may be installed without adding a moving components to the existing HVAC system. Further, the components of the sterilizing unit provide minimum obstruction to airflow. In various embodiments, a UV absorbent screen may be installed at the discharge grate of an HVAC system in which the sterilizing unit has been installed. In this manner, harmful UV radiation may be contained within the HVAC duct. The escape of any UV radiation outside the intended radiation zones may be prevented. In various embodiments, the components of the sterilizing unit may be mounted in a modular unit cartridge that may be sized to slide into a standard air duct for easy installation into an HVAC. The electronics for the components of the sterilizing unit (e.g., for the LEDs) may be enclosed within center bodies of the units, and only require only one low wattage AC line to supply power. In some embodiments, an interlock switch may be installed in the HVAC system in order to disable the sterilizing unit when the duct is accessed. Further, a UV sensor may be incorporated into the duct in order to ensure that the sterilizing unit is operating normally.

FIG. 1A illustrates an example HVAC system 100 according to various embodiments. The HVAC system 100 may include an inlet duct 102 that receives a supply airflow, and a filter 104 to remove large dust and particulate matter from the supply airflow. An air handler 106 in the HVAC system 100 may include a fan 108, heating element 110, cooling element 112, and control electronics 114. In various embodiments, the fan 108 may be a blower fan, and the cooling element 112 may be an evaporator coil. For example, a compressor 116 located external to the system may move chilled refrigerant into the evaporator coil. As the airflow moves over the evaporator coil, the chilled refrigerant may remove the heat from the air. Once the refrigerant is warmed through the transfer of heat from the air to the evaporator coil, the refrigerant may be returned from the evaporator coil to a condenser coil in the compressor 116. The cooling element 112 may optionally include a heat pump to reverse the process in order to heat the airflow. In particular, such reversal may involve the refrigerant in the evaporator coil expelling heat into the airflow. Further, one or more heating element 110 included in the air handler 106 may supply heat when temperatures fall below a certain point. In various embodiments, a thermostat 118 in the building or room may be coupled to the control electronics 114 of the air handler 106.

In various embodiments, heated or cooled air from the air handler 106 may be provided to a ductwork system 120, and vented into the interior of a room or other space through outlet vents 122a, 122b, 122c. In some embodiments, each of a plurality of rooms may be configured to receive heated or cooled air from the HVAC system 100 through one of the outlet vents 122a, 122b, 122c.

Figure 1B:
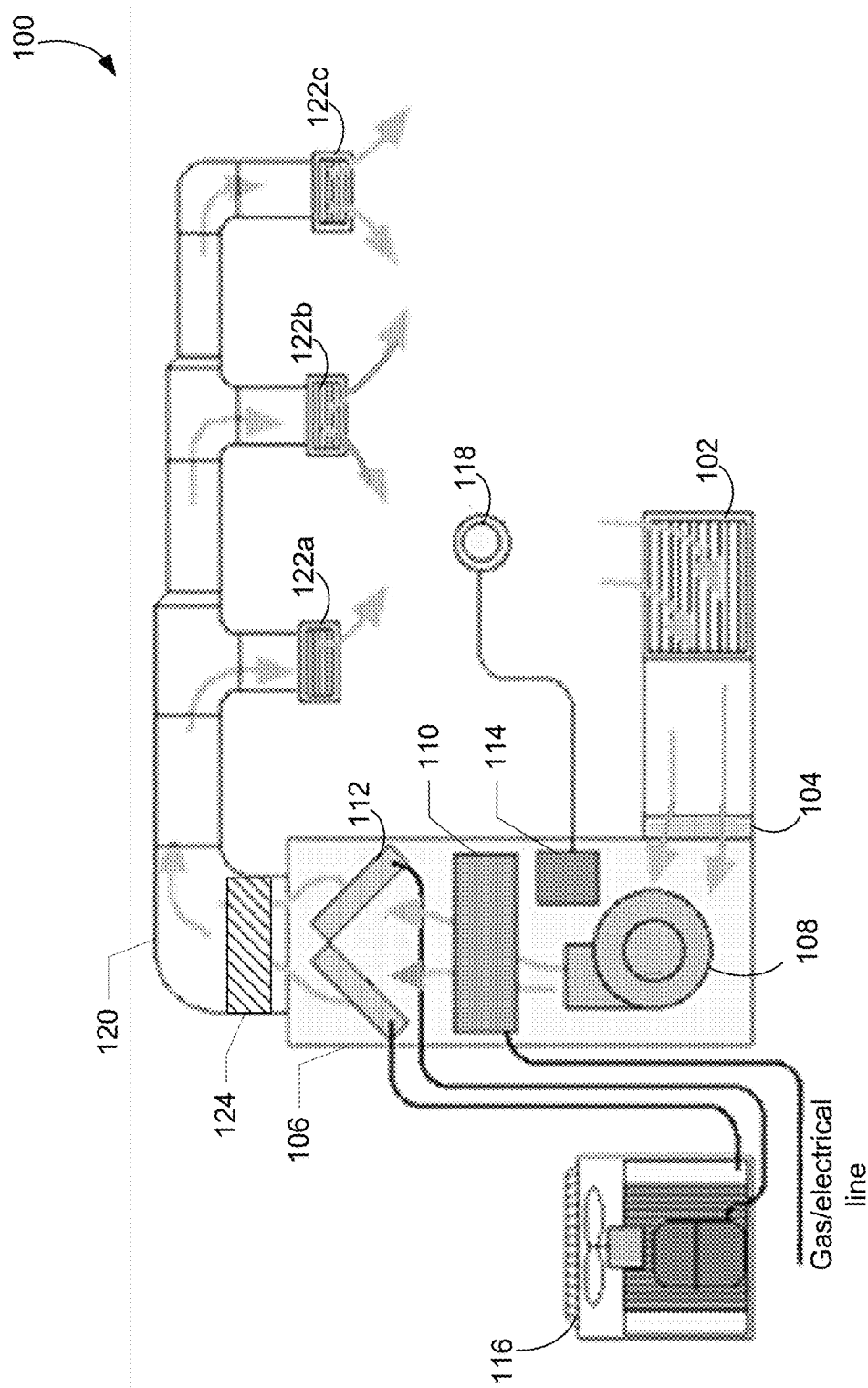
Figure 2:
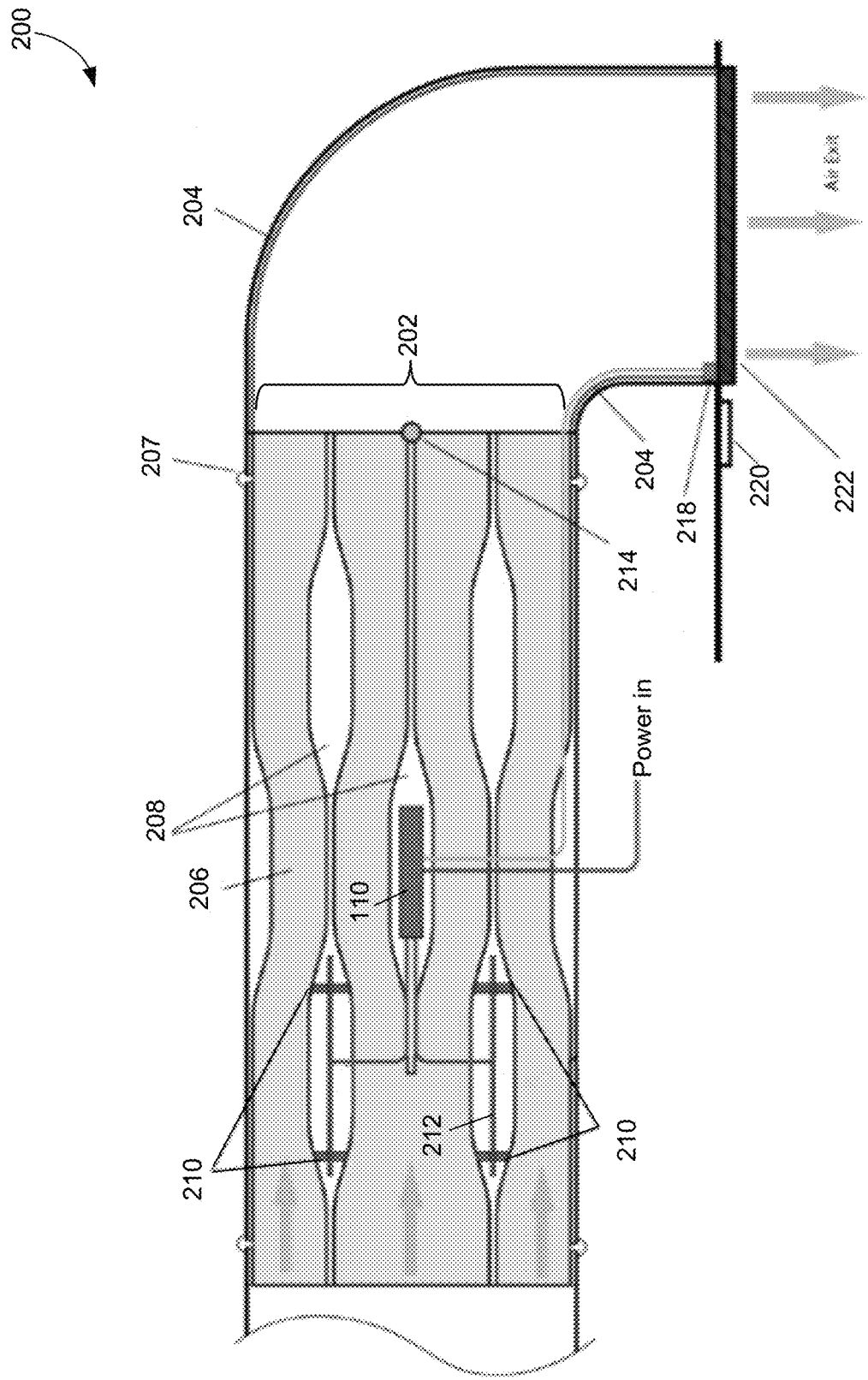
FIG. 2 is a cutaway view of a sterilizing unit installed within an HVAC system according to various embodiments.

According to various embodiments, the HVAC system 100 may be configured with components designed to fit into the existing ductwork to effectively sanitize the air flow. In some embodiments, sterilizing components may be installed at the duct position of block 124 and/or at one or more outlet vent 122a-122c. In some embodiments, sterilizing components may additionally or alternatively be installed at the duct position of blocks 126, 128. In order to maintain consistent airflow pressure through outlet vent 122a-122c, blocks 124, 126, and 128 may be sized with sequentially smaller cross-sectional areas so as to increase airflow pressure despite the increasing distance away from air handler 106. In another embodiment, illustrated in FIG. 1B, a sterilizing component may be installed at a central duct position represented by block 124. FIG. 2 is a diagram illustrating components of an example HVAC system 200 that is suitable for implementing a sterilizing unit according to various embodiments. With reference to FIGS. 1A-2, the HVAC system 200 may represent one or more portion of the HVAC system 100 as described. For example, a sterilizing unit 202 may be inserted into a duct 204 (e.g., at position 124, 126, 128 of ductwork system 120). The HVAC system 200 may direct an air stream (depicted by arrows) through the duct 204.

In various embodiments, the duct 204 may have standardized or customized dimensions. In various embodiments, the duct 204 may be variously shaped based on the existing HVAC system design, and may include one or more bend in proximity to the air exit.

The sterilizing unit 202 may include a UV reflective chamber 206 that is inserted into the duct 204 through which air flows in the regular operation of the HVAC system. The UV reflective chamber 206 may be lined with a UV reflective coating, and may be attached to duct 204 by one or more fastener 207. The sterilizing unit 202 may also include a plurality of center bodies 208 within the UV reflective chamber 206, which may be hollow areas positioned within the air flow through the duct 204. The number and shape of the center bodies 208 incorporated into the sterilizing unit 202 may depend on the dimensions of the UV reflective chamber 206 and the duct 204 into which the sterilization unit 202 may be installed. For example, as shown in FIG. 2, the sterilizing unit 202 may include five center bodies 208. The center bodies 208 may be cylindrical or approximately cylindrical in shape. In various embodiments, the outer surfaces of the center bodies 208 may be coated with a UV reflective material. The center bodies 208 may be hollow structures.

In various embodiments, at least one UV LED 210 may be mounted on the outside of one or more center body 208. In other embodiments, an array of UV LEDs 210 may be mounted on the outside of one or more center bodies 208. The number of UV LEDs in each array, and the number and location of the center bodies 208 onto which they mounted, may be customized based on the size of the sterilizing unit 202 and the duct 204 into which the sterilization unit 202 may be installed. For example, in sterilizing unit 202, the two center bodies 208 that are positioned farthest from the air exit of the duct 204 may each be configured with an array of four UV LEDs 210. Each of the center bodies 208 having UV LEDs 210 may house a printed circuit board assembly (PCBA) 212, which may be powered by a power supply 110 housed within a different center body 208. In various embodiments, the power supply 110 may include various sub-components and features as would be necessary to provide and regulate power to the various components In various embodiments, the sterilizing unit 202 may include at least one UV sensor 214 positioned at the end of the UV reflective chamber 206 that is closest to the air exit end of the duct 204. In some embodiments, the UV sensor 214 may be coupled to a UV function display 220 that positioned outside of the duct 104 in order to provide feedback to a user and ensure normal operation without requiring disassembly of the sterilizing unit 202. The HVAC system 200 may also include an interlock switch 218 to disable the sterilizing unit 212 when the duct 204 is accessed.

In various embodiments, the portion of the duct 204 between the sterilizing unit 206 and the air exit may be coated with a UV absorbent material. The UV absorbent material may be, for example, a layer that includes titanium dioxide and/or zinc oxide. In some embodiments, the exit from the duct 204 may also be covered with a UV absorbent screen 222 also made of any of a variety of UV absorbent materials.

In various embodiments, a duct may be variously shaped to satisfy treatment and design needs. The center bodies may be positioned such that the incoming air stream flow from the upstream HVAC system achieves optimum exposure to the UV radiation via the UV reflective material on the exterior surface of the downstream center bodies and lining the sterilizing unit 102.

The sterilizing units according to various embodiments may be extendable and repeatable such that an HVAC system may have multiple sterilizing units 202 according to the existing ductwork system and the particular sterilizing needs. In some embodiments, one or more sterilizing units 202 may be installed close to the HVAC center so the air flow is treated at the source before going to other areas of the building. In some embodiments, sterilizing units may be put into multiple, different ducts in an HVAC system, such as on each floor of a building. The sterilizing unit(s) may be used for airflow systems in residences, commercial buildings, hospitals, public spaces, and other environments where it is desired to deliver clean, pure airflow.

In various embodiments, the UV radiation may be provided by UV light emitting diodes (LEDs) 210 that are attached to one or more center body 208.

Another embodiment of the present invention discloses a kit for retrofitting an existing duct of an HVAC system with at least one sterilizing unit to output clean air to a building. For example, the sterilizing unit 202 may be a modular unit that may be installed within existing HVAC ductwork 204. In other embodiments, section of existing HVAC ductwork 204 may be removed and replaced with the sterilizing unit 202.

In some embodiments, a portion of the existing duct in the HVAC system may be removed and discarded or recycled. The sterilizing unit 202 described above would then be installed such that the outer housing is sealably coupled to the existing duct 204, and the power supply 110 to power the PCBA(s) 212 may be electrically connected to an existing electrical supply of the device. Such connections may be provided using mechanical and electrical components of the kit's hardware kit. Mechanical components may include, but are not limited to, screws, nuts, bolts, washers, seals, gaskets, caps, and connectors. Electrical components may include, but are not limited to, cables, wire harnesses, electrical connectors, switches, circuit boards, circuit breakers, and fuses.

In various embodiments, adaptors various mechanical interfaces may be incorporate as components in a hardware kit, as will be readily appreciated by one having skill in the art. Male-Female couplings, gaskets, reducers, expanders, and clamps are all examples of adaptors that may be chosen as the first and second adaptor means.

In various embodiments, the power supply for providing power to the PCBA(s) 212 and UV LEDs 210 may include a regulation means. The power supply 110 may be, but is not limited to, a power plug, a voltage regulator, a transformer, a circuit breaker, and/or other circuitry for powering, monitoring, and regulating the UV LEDs 210 through one or more PCBA 212. In some embodiments, the power supply 110 may be a rechargeable battery pack that is e electrically connected to the HVAC system in order to provide power to the PCBA(s) 212 and UV LEDs 210. The battery pack may be recharged by conventional charging means, as is known in the art.

In various embodiments, the interlock switch 218 may serve to shut off the UV LEDs 210 in a sterilizing unit 202 if any part of the duct 204 in which the sterilizing unit 202 is installed were to become open. In this manner, a user may be protected from exposure to potentially harmful UV radiation. The interlock switch 218 may include various components known in the art including, but not limited to, relays, contact closures, and circuit breakers.

As will be clear to those of ordinary skill of the art, as well as within the scope and of this disclosure, that while the above embodiments have been described as a UV sanitization unit apparatus installed to clean the airflow within an HVAC system, it may equivalently be installed in other systems Further, various embodiments may comprise one or more than one of any component. For example, in addition to the embodiments described above, various embodiments may include a first sterilizing unit at one end of a duct, and a second sterilizing unit at another end of the same duct. No additional fans or filters beyond the existing HVAC system are needed to achieve clean air according to various embodiments.

Referring to FIG. 1, the sterilizing unit 202 may be comprised of a hollow cross sectional area which is extruded to a desired length to match a removable portion of a duct in the HVAC system, and to provide a UV reflective material and a plurality of center bodies. Embodiments of the sterilizing unit 202 may comprise an inner surface treatment that provides for a diffuse reflection of the UV radiation. The use of diffuse reflectors may increase the efficiency of the UV irradiation field by scattering the UV light rays, as opposed to specular reflective surfaces (such as polished metals) that reflect the UV ray at an angle equal to the angle at which the ray hits the surface. In some embodiments, a diffuse UV reflective surface may be accomplished through a microtexture, a coating, or a laminated material, such as polytetrafluoroethylene (PTFE).

An embodiment of the sterilizing unit 202 may comprise a cross-sectional area that is substantially consistent throughout the length of the airflow and irradiation management chamber. A further embodiment of the sterilizing unit may comprise a cross-sectional area that varies in shape and/or size throughout the length of the airflow and irradiation management chamber. The cross section of the one or more sterilizing unit may be circular, elliptical, rectangular, or any other shape as may be chosen to optimize the path of the airflow through the desired duct size. Each sterilizing unit may be designed to sustain a specific volumetric throughput.

Embodiments of the HVAC system may include ducts that are substantially straight, substantially curved, or comprised of a combination of substantially straight and curved sections.

The sterilizing unit 202 itself may be manufactured utilizing various methods and materials as may be known in the art including, but not limited to, extruded plastics, formed metals, or a combination of materials. The wall of the duct 204 through which air flows downstream from a sterilizing unit may have an inner surface that blocks UV light.

The UV LEDs 210 that in various embodiments may be selected based upon the desired wavelength and power rating, as well as size and expected lifespan. The number and distribution of these UV LEDs 210 on the center bodies 208 within a sterilizing chamber 206 may be such as to maximize the radiant flux within the sterilizing chamber, while preventing substantial UV radiation escape from the duct.

The various electrical components, such as the PCBAs 212 for the UV LEDs 210, the interlock switch 218, the UV sensor 214, and the UV function display 220, may be electrically connected to and powered by the power supply 110. The power supply 110 may further comprise one or more of an electronics and control module, processing means, and power regulation means.

Embodiments of the present invention may comprise a system for supplying clean air to one or more room in a building. Embodiments of the system may comprise: at least one sterilizing unit 202 including a plurality of UV LEDs 210 capable of achieving at least a baseline kill rate of airborne pathogens.

Other embodiments provide an effective, safe, and convenient methods for substantially eliminating airborne pathogens by retrofitting a sterilizing unit 202 within an existing HVAC system to create an air treatment system. The air treatment system may be compact and quiet, and may be configured for use with any of a variety of present or future devices that indirectly supply heated air to a patient.

The HVAC system 100 may include an intake area 102 with an opening to the surrounding air. Air that passes through the opening 102 of the HVAC system 100 may be filtered and/or pushed by an existing fan prior to passing through the one or more sterilizing unit 202 for purification.

In various embodiments, the duct 204 including a sterilizing unit 202 may include at least one bend after the location of the sterilizing unit 202, forming a shape that is configured to further prevent spurious UV radiation from escaping the sterilizing unit 202 while providing the airflow with sufficient UV radiation dosage to achieve a desired kill rate.

In some embodiments, the UV LEDs 210 in the at least one array emit radiation at one or more wavelength within the range of 240-280 nm, such as within the range of 260-270 nm.

The internal surface of one or more section of the sterilizing chamber 206 may be coated with a reflective material.

In various embodiments, the configuration of at least one sterilizing chamber 206 installed within a duct 204 may be designed to manage the UV radiation flux and effectively sanitize the airflow without compromising the desired airflow rate. Generally, increasing the length of the pathway may lead to longer residence time for the airflow, and therefore providing space for more center bodies configured with UV LED 210 arrays to increase effectiveness of the UV radiation in killing airborne pathogens. However, since such increases lengthen the path of the airflow also increases the pressure drop over the system, the sterilizing unit may be designed with a length to mitigate such pressure drop. Also, while a high level of reflectance within the sterilizing unit generally maximizes the effectiveness of the UV LEDs 210, the sterilizing unit may be designed and positioned to prevent reflected radiation from escaping the duct.

In various embodiments, the power supply driving the PCBAs 212 and UV LEDs 210 may be separated from the airflow by being housed within a center body. Such power supply may include conventionally available power supplies and may contain a circuit breaker.

The center bodies 208 with UV LEDs 210 may be positioned to obtain the maximum amount of UV reflectance based on the configuration of the duct in which the sterilizing unit is installed, as well as to avoid escape of the UV radiation from the duct. In various embodiments, such positioning may be obtained using UV radiation ray tracing technology.

The UV reflective chamber (e.g., 206) in various embodiments may be formed by coating an interior surface(s) of the sterilizing chamber (e.g., 202) with a highly reflective material, such as polished aluminum.

In some embodiments, the airflow of the air treatment device 100 may be within the range of about 100 cubic feet per minute (cfm) to about 700 cfm. In some embodiments, the air treatment device 100 may be configured such that the pressure drop is substantially unchanged from that of the existing airflow through the HVAC system.

An electronics and control module may be incorporated to regulate power supplied to various components in embodiment HVAC systems. In some embodiments, an electronics and control module may be configured to be external to the duct(s) in which one or more sterilizing unit is installed. The electronics and control module may be provided as one or multiple units/integrated circuits, and may be coupled to the power supply for one of more sterilizing unit 202, UV sensor 214, UV function display 220, and interlock switch 218.

Figure 3:
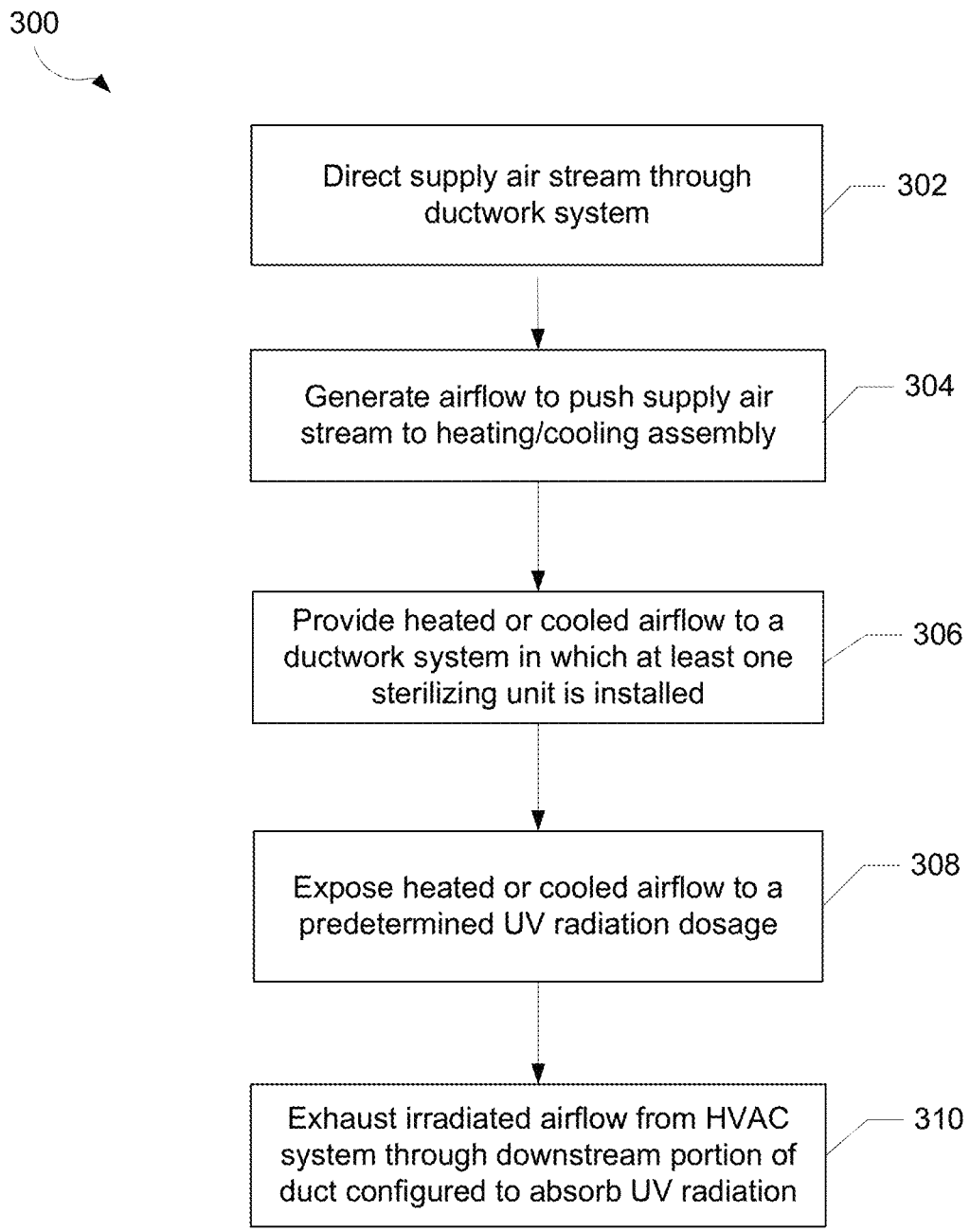
FIG. 3 is a process flow diagram illustrating a method for reducing airborne pathogens contaminants in an airflow within an HVAC system according to various embodiments.

FIG. 3 shows an embodiment method 300 for purifying air that is provided to a building or room through an HVAC system (e.g., system 100 of FIG. 1) to achieve the selected temperature conditions. Referring to FIGS. 1A-3, in block 302, a supply air stream may be directed through a ductwork system. For example, the supply air stream, which may be a combination of fresh air and return air, may enter the HVAC system (e.g., 100) through an inlet duct. In some embodiments, the supply air stream may pass through at least one filter that removes fine particulates (e.g., HEPA filter) and/or that adsorbs harmful gasses (e.g., volatile organic chemical filter). In block 304, an airflow may be generated to push the supply air stream to a heating/cooling assembly. In various embodiments, the airflow may be generated by a fan (e.g., 108), and the heating/cooling assembly may include an air handler (e.g., 106) that blows the airflow through one or more evaporator coil that heats or cools the airflow as required. In block 306, the heated or cooled airflow may be provided to a ductwork system in which at least one sterilizing unit (e.g., 202) is installed. In various embodiments, the ductwork system may be configured to distribute air throughout the home or building, and may include one or a plurality of sterilizing units.

In block 308, the heated or cooled airflow may be exposed to a predetermined UV radiation dosage by passing through the UV reflective chamber (e.g., 206) of one or more sterilizing unit (e.g., 204). For example, where multiple portions of a main duct (e.g., 120) branch off to separate rooms, one or more sterilizing unit may be installed along the main duct, or each branched portion of the duct may include a separate sterilizing unit. In various embodiments, the shape and size of the sterilizing unit(s), and the position of the UV LEDs within the UV reflective chamber(s), may be configured to prevent spurious UV radiation outside of the duct.

The predetermined UV radiation dosage may be achieved by optimizing the number and position of the UV LED arrays, such as on one or more center body, and the materials used, and configuring the sterilizing unit to allow for a necessary residence time. In various embodiments, the predetermined UV radiation dosage may be sufficient to kill or disable at least 90% of airborne pathogens within the airflow.

In block 310, the irradiated airflow may be exhausted from the HVAC system through a downstream portion of the duct(s) configured to absorb UV radiation. For example, the downstream portion of the duct may be lined with UV absorbing material. in some embodiments, the irradiated airflow may pass through a UV absorbent screen (e.g., 222) that covers one or more air outlet vent (e.g., 122).

In some embodiments, additional air treatment functionality may be added to an HVAC system by including specialized components. For example, a UV sensor (e.g., 214) may be disposed within the in or connected to a sterilizing unit of embodiment systems in order to monitor the radiation flux and ensure proper operation. In various embodiments, such UV sensor may use one or more UV photodetector, such as those based on gallium nitride (GaN), indium gallium nitride (InGaN), and/or aluminum gallium nitride (AlGaN) materials. In various embodiments, the UV sensor may be configured to communicate with an externally visible indicator (e.g., UV function display 220) to confirm to the user that the device is working. In some embodiments, the indicator may be in wireless communication with one or more UV sensor connected to the one or more sterilizing unit.

Figure 4:
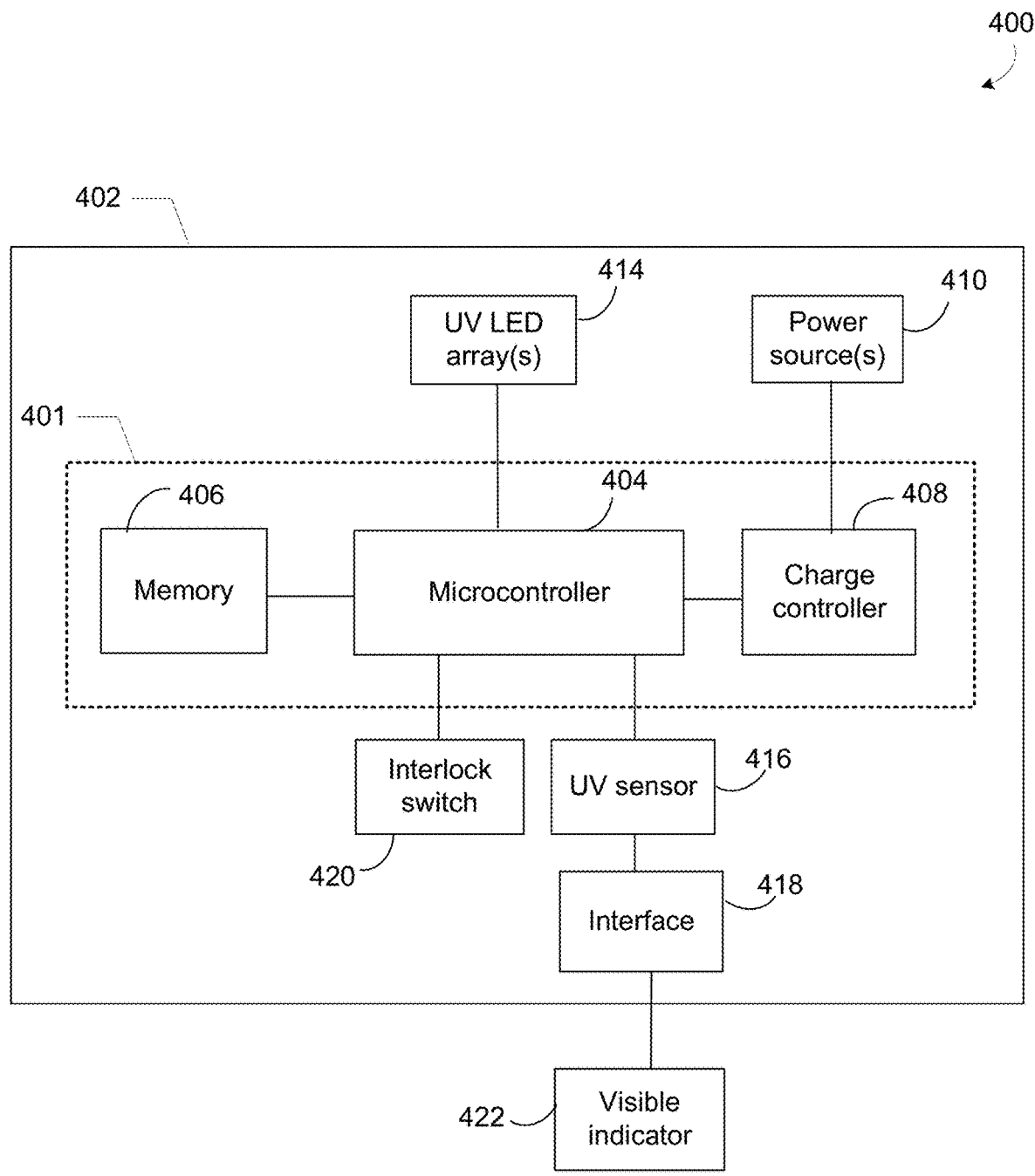
FIG. 4 is a component block diagram of an HVAC system including a sterilizing unit according to various embodiments.

FIG. 4 illustrates air treatment components of an example HVAC system 400. In system 400, at least one electronics and control module 401 may be implemented on a circuit board (e.g., PCBA(s) 209) within a sterilizing unit 402, such as within one or more center body (e.g., 208). With reference to FIGS. 1A-4, the circuit board may be located within one or more center body (e.g., 208), and may be separate from one or more controller for the other components of the HVAC system.

The electronics and control module 402 may include a microcontroller 404 coupled to a memory device 406 and a charge controller 408. The charge controller 808 may connect to at least one power source 410, which may be an AC power supply and/or a battery. Other air treatment components within the HVAC system 400 may include one or more UV LED array 414, a UV sensor 416, and an interlock switch 420. The interlock switch 420 may be coupled to the microcontroller 404. The UV sensor 416 may be connected to an interface 418 that connects one or more visible indicator 422. The visible indicator 422 may be provided as an external component, which may be part of another device or system (e.g., a smartphone, tablet, etc.). The interface 418 may connect the visible indicator 822 through a wireless communication link.

Referring to all drawings and according to various embodiments of the present disclosure, a sterilizing unit configured to treat air circulating in a heating, ventilation, and air conditioning (HVAC) system is provided. The sterilizing unit 202 may include a portion of a duct 204 at least partially lined with an ultraviolet (UV) reflective material; a plurality of center bodies 208 positioned within the portion of the duct 204, each comprising an external UV reflective surface; and at least one array of UV light emitting diodes (LEDs) 210 mounted on a surface of at least one of the plurality of center bodies 208; wherein the sterilizing unit 202 is configured to replace a section of an existing duct in the HVAC system such that airflow within the HVAC system passes through the sterilizing unit 202 before exiting from one or more vent.

In an embodiment, the sterilizing unit 202 may further include a power supply 110 housed within at least one of the center bodies 208. In one embodiment, the sterilizing unit 202 may include at least one array of UV LEDs, wherein each array of UV LEDs is connected to a printed circuit board assembly (PCBA) 212 within the center body 208 on which the array is mounted. In one embodiment, the sterilizing unit 202 may include at least one center body 208 upon which the at least one array of UV LEDs 210 is mounted is positioned at an end of the sterilizing unit 202 upstream from an airflow exit point. In one embodiment, the sterilizing unit 202 may include at least one array of UV LEDs that is configured to emit radiation at one or more wavelength within a range of 240-280 nm. In one embodiment, the sterilizing unit 202 may include UV LEDs 210 that are configured to irradiate the air circulating within the HVAC system with a UV radiation dosage sufficient to reduce airborne pathogens.

In another embodiment, a HVAC system may be provided. The HVAC system may include a ductwork system 120; at least one sterilizing unit 202 installed into the ductwork system 120, wherein each of the at least one sterilizing unit 202 includes: a portion of a duct 204 at least partially lined with an ultraviolet (UV) reflective material; a plurality of center bodies 208 positioned within the portion of the duct 204, each comprising an external UV reflective surface; and at least one array of UV light emitting diodes (LEDs) 210 mounted on a surface of at least one of the plurality of center bodies 208, wherein the at least one sterilizing unit 202 is configured to receive an airflow; at least one UV sensor 214 coupled to each of the at least one sterilizing unit 202, wherein the at least one UV sensor 214 is configured to monitor performance of the UV LEDs 210; and a UV absorbent screen 222 positioned at least one airflow outlet.

In one embedment, the HVAC system may further include at least one interlock switch 218 configured to disable operation of the at least one sterilizing unit 202. In one embodiment, the HVAC system may include at least a section of the ductwork section downstream from one of the at least one sterilizing unit 202 that is lined with a UV absorbent material. In one embodiment, the HVAC system may include at least one UV sensor 214 that is positioned between the sterilizing unit 202 and one of the at least one airflow outlet. In one embodiment, the HVAC system may include at least one array of UV LEDs 210 that is configured to emit radiation at one or more wavelength within a range of 240-280 nm. In one embodiment, the HVAC system may include UV LEDs 210 that are configured to irradiate the airflow with a UV radiation dosage sufficient to reduce airborne pathogens. In one embodiment, the HVAC system may also include a visible indicator 220 configured to provide information to a user about performance of the UV LEDs 210 within the at least one sterilizing unit 202.

The UV LEDs of the one or more array may be electrically connected to the electronics and control module and fixedly attached to mated openings in the walls of a portion of the sterilizing chamber (e.g., straight region) such that the UV LED array circuit boards are outside of the sterilizing chamber and the UV LEDs irradiate inside the sterilization region of the sterilizing chamber. The UV sensor may be electrically connected to the electronics and control module and fixedly attached to a mated opening in the wall of the sterilizing chamber such that the sensor can detect irradiance levels.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the following claims.

What is claimed is:

1. A sterilizing unit configured to treat air circulating in a heating, ventilation, and air conditioning (HVAC) system, comprising:
    a portion of a duct at least partially lined with an ultraviolet (UV) reflective material;
    a plurality of center bodies positioned within the portion of the duct, wherein each of the plurality of center bodies comprises:
    a hollow structure that is approximately cylindrical in shape; and
    a UV reflective material coating an outer surface of the hollow structure;
    at least one array of UV light emitting diodes (LEDs) mounted on the outer surface of at least one of the plurality of center bodies; and
    a power supply housed within another one of the plurality of center bodies, wherein the other one of the plurality of center bodies does not have UV LEDs mounted on the outer surface;
    wherein the sterilizing unit is configured to replace a section of an existing duct in the HVAC system such that airflow within the HVAC system passes through the sterilizing unit before exiting from one or more vent.

2. The sterilizing unit of claim 1, wherein each of the at least one array of UV LEDs is connected to a printed circuit board assembly (PCBA) within the center body on which the array is mounted.

3. The sterilizing unit of claim 1, wherein the first center body is positioned at an end of the sterilizing unit upstream from an airflow exit point.

4. The sterilizing unit of claim 1, wherein the at least one array of UV LEDs is configured to emit radiation at one or more wavelength within a range of 240-280 nm.

5. The sterilizing unit of claim 1, wherein the UV LEDs are configured to irradiate the air circulating within the HVAC system with a UV radiation dosage sufficient to reduce airborne pathogens.

6. A heating, ventilation, and air conditioning (HVAC) system, comprising:
    a ductwork system;
    at least one sterilizing unit installed into the ductwork system, wherein each of the at least one sterilizing unit comprises:
    a portion of a duct at least partially lined with an ultraviolet (UV) reflective material;

a plurality of center bodies positioned within the portion of the duct, wherein each of the plurality of center bodies comprises:
a hollow structure that is approximately cylindrical in shape; and
a UV reflective material coating an outer surface of the hollow structure;
at least one array of UV light emitting diodes (LEDs) mounted on the outer surface of at least one of the plurality of center bodies; and
a power supply housed within another one of the plurality of center bodies, wherein the other one of the plurality of center bodies does not have UV LEDs mounted on the outer surface;
wherein the at least one sterilizing unit is configured to receive an airflow;
at least one UV sensor coupled to each of the at least one sterilizing unit, wherein the at least one UV sensor is configured to monitor performance of the UV LEDs; and
a UV absorbent screen positioned at least one airflow outlet.

7. The HVAC system of claim 6, further comprising at least one interlock switch configured to disable operation of the at least one sterilizing unit.

8. The HVAC system of claim 6, wherein at least a section of the ductwork section downstream from one of the at least one sterilizing unit is lined with a UV absorbent material.

9. The HVAC system of claim 6, wherein each of the at least one UV sensor is positioned between the sterilizing unit and one of the at least one airflow outlet.

10. The HVAC system of claim 6, wherein the at least one array of UV LEDs is configured to emit radiation at one or more wavelength within a range of 240-280 nm.

11. The HVAC system of claim 6, wherein the UV LEDs are configured to irradiate the airflow with a UV radiation dosage sufficient to reduce airborne pathogens.

12. The HVAC system of claim 6, further comprising a visible indicator configured to provide information to a user about performance of the UV LEDs within the at least one sterilizing unit.

* * * * *